(12) United States Patent
Franklin et al.

(10) Patent No.: US 8,304,420 B2
(45) Date of Patent: Nov. 6, 2012

(54) SUBSTITUTED QUINAZOLINES FOR REDUCING PLATELET COUNT

(75) Inventors: Richard Franklin, Hampshire (GB); Bernard T. Golding, Newcastle upon Tyne (GB); Peter A. Cicala, Flemington, NJ (US)

(73) Assignee: Shire LLC, Florence, KY (US)

( * ) Notice: Subject to any disclaimer, the term of this patent is extended or adjusted under 35 U.S.C. 154(b) by 0 days.

(21) Appl. No.: 11/946,536

(22) Filed: Nov. 28, 2007

(65) Prior Publication Data

US 2008/0176875 A1     Jul. 24, 2008

Related U.S. Application Data

(60) Provisional application No. 60/861,578, filed on Nov. 28, 2006.

(51) Int. Cl.
*A61K 31/517* (2006.01)
(52) U.S. Cl. ..................... 514/266.4; 544/292
(58) Field of Classification Search ............... 514/266.4; 544/292
See application file for complete search history.

(56) References Cited

U.S. PATENT DOCUMENTS

| | | |
|---|---|---|
| 1,947,926 A | 2/1934 | Steindorff et al. |
| 2,256,999 A | 9/1941 | Castner |
| 2,469,695 A | 5/1949 | McNally |
| 2,608,584 A | 8/1952 | Sprules et al. |
| 2,732,403 A | 1/1956 | Surrey |
| 2,862,966 A | 12/1958 | Surrey |
| 2,883,435 A | 4/1959 | Welch |
| 3,313,854 A | 4/1967 | Levy |
| 3,928,476 A | 12/1975 | Shimada et al. |
| 3,932,407 A | 1/1976 | Beverung, Jr. et al. |
| 3,983,119 A | 9/1976 | Beverung, Jr. et al. |
| 3,983,120 A | 9/1976 | Beverung et al. |
| 3,988,340 A | 10/1976 | Partyka et al. |
| 4,036,838 A | 7/1977 | Vogel et al. |
| 4,048,168 A | 9/1977 | Yamamoto et al. |
| 4,146,718 A | 3/1979 | Jenks et al. |
| 4,179,560 A | 12/1979 | Yamamoto et al. |
| 4,202,974 A | 5/1980 | Yamamoto et al. |
| 4,208,521 A | 6/1980 | Crenshaw et al. |
| 4,256,748 A | 3/1981 | Chodnekar et al. |
| 4,357,330 A | 11/1982 | Fleming, Jr. et al. |
| 4,390,540 A | 6/1983 | Chodnekar et al. |
| 4,444,777 A | 4/1984 | Fleming, Jr. et al. |
| RE31,617 E | 6/1984 | Beverung, Jr. et al. |
| 4,455,311 A | 6/1984 | Kienzle et al. |
| 4,610,987 A | 9/1986 | Ishikawa et al. |
| 4,663,320 A | 5/1987 | Jones et al. |
| 4,670,434 A | 6/1987 | Venuti |
| 4,808,405 A | 2/1989 | Smith et al. |
| 4,837,239 A | 6/1989 | Benjamin et al. |
| 4,847,276 A | 7/1989 | Yarrington |
| 4,904,667 A | 2/1990 | Demers et al. |
| 5,043,327 A | 8/1991 | Freyne et al. |
| 5,133,972 A | 7/1992 | Ferrini et al. |
| 5,306,709 A | 4/1994 | Gewirtz |
| 5,334,384 A | 8/1994 | Mannix et al. |
| 5,391,737 A | 2/1995 | Reiter et al. |
| 5,801,245 A | 9/1998 | Lang |
| 5,874,437 A | 2/1999 | Garvey et al. |
| 6,024,975 A | 2/2000 | D'Angelo et al. |
| 6,037,346 A | 3/2000 | Doherty, Jr. et al. |
| 6,110,471 A | 8/2000 | Conti et al. |
| 6,156,753 A | 12/2000 | Doherty, Jr. et al. |
| 6,194,420 B1 | 2/2001 | Lang |
| 6,221,383 B1 | 4/2001 | Miranda et al. |
| 6,297,243 B1 | 10/2001 | Groendahl |
| 6,299,900 B1 | 10/2001 | Reed et al. |
| 6,331,543 B1 | 12/2001 | Garvey et al. |
| 6,376,242 B1 | 4/2002 | Hanson |
| 6,388,073 B1 | 5/2002 | Lang et al. |
| 6,403,597 B1 | 6/2002 | Wilson et al. |
| 6,548,490 B1 | 4/2003 | Doherty, Jr. et al. |
| 6,548,529 B1 | 4/2003 | Robl et al. |
| 6,585,995 B1 | 7/2003 | Hanson |
| 6,653,500 B2 | 11/2003 | Lang et al. |
| 7,700,608 B2 | 4/2010 | Franklin |
| 7,910,597 B2 | 3/2011 | Franklin |
| 2002/0004056 A1 | 1/2002 | Hayashi et al. |
| 2002/0004065 A1 | 1/2002 | Kanios et al. |
| 2002/0004498 A1 | 1/2002 | Doherty et al. |

(Continued)

FOREIGN PATENT DOCUMENTS

AT    A2732004    8/2005

(Continued)

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, p. 18.*
Agrylin Monograph—Shire 2003—10.
Cohen-Solal et al., Thromb. Haemost. 1997, 78:37-41—p. 18, I 31 of 5096 and p. 27, I 9 of 3796.
Cramer et al., Blood, 1997, 89:2336-46—p. 18, I 31 of 5096 and p. 27, I 9 of 3796.
Kienzle et al., "1,5-Dihydroimidazoquanizolinones as blood platelet aggregation inhibitors," Eur. J. Med. Chem. Chim. Ther., 1982, 17:547-556.

(Continued)

*Primary Examiner* — Douglas M Willis

(74) *Attorney, Agent, or Firm* — Frommer Lawrence & Haug LLP; Shelly M. Fujikawa

(57) ABSTRACT

This invention relates to the discovery of prodrugs of 3-or 5-substituted analogues of the selective platelet lowering agent anagrelide which have reduced potential for cardiovascular side-effects and which should therefore lead to improved patient compliance and safety in the treatment of myeloproliferative diseases. More specifically, the present invention relates to prodrugs of certain imidazoquinazoline derivatives which have utility as platelet lowering agents in humans. The compounds of the present invention function by inhibiting the formation of blood platelets. An example of a compound of the present invention is methyl 2-(2-amino-5,6-dichloroquinazolin-3 (4H)-yl)-2-methylpropanoate or the 3,3-demethyl anagrelide open-ringed analog.

10 Claims, 1 Drawing Sheet

U.S. PATENT DOCUMENTS

| | | | |
|---|---|---|---|
| 2003/0114673 A1 | 6/2003 | Lang | |
| 2003/0134861 A1 | 7/2003 | Doherty et al. | |
| 2003/0181461 A1 | 9/2003 | Lautt et al. | |
| 2004/0014761 A1 | 1/2004 | Place et al. | |
| 2004/0087486 A1 | 5/2004 | Hanson | |
| 2004/0087546 A1 | 5/2004 | Zeldis | |
| 2004/0209907 A1 | 10/2004 | Franklin | |
| 2005/0049293 A1 | 3/2005 | Lautt | |
| 2005/0119272 A1 | 6/2005 | Lautt et al. | |
| 2005/0228001 A1 | 10/2005 | Hanson | |
| 2006/0030574 A1 | 2/2006 | Franklin | |
| 2006/0052601 A1 | 3/2006 | Franklin | |
| 2006/0148832 A1* | 7/2006 | Sachse | 514/266.4 |
| 2006/0292213 A1 | 12/2006 | Gerber et al. | |
| 2007/0066619 A1 | 3/2007 | Hamilton et al. | |
| 2007/0099819 A1 | 5/2007 | Glidden | |
| 2010/0137343 A1 | 6/2010 | Franklin | |
| 2011/0065714 A1 | 3/2011 | Golding et al. | |
| 2011/0065735 A1 | 3/2011 | Golding et al. | |
| 2011/0071171 A1 | 3/2011 | Golding et al. | |
| 2011/0071172 A1 | 3/2011 | Golding et al. | |
| 2011/0071173 A1 | 3/2011 | Golding et al. | |
| 2011/0071174 A1 | 3/2011 | Golding et al. | |
| 2011/0086851 A1 | 4/2011 | Golding et al. | |
| 2011/0130405 A1 | 6/2011 | Golding et al. | |
| 2011/0130413 A1 | 6/2011 | Golding et al. | |
| 2011/0152298 A1 | 6/2011 | Golding et al. | |
| 2011/0263850 A1 | 10/2011 | Golding | |

FOREIGN PATENT DOCUMENTS

| | | |
|---|---|---|
| CA | 2150033 | 6/1994 |
| DE | 2832138 A1 | 2/1979 |
| DE | 19935209 | 2/2001 |
| EP | 0008408 A | 3/1980 |
| EP | 0 021 338 | 1/1981 |
| EP | 0029559 A | 6/1981 |
| EP | 0046267 | 2/1982 |
| EP | 0054180 | 6/1982 |
| EP | 0 153 152 | 8/1985 |
| EP | 0 205 280 | 12/1986 |
| EP | 0 406 958 | 1/1991 |
| EP | 0 514 917 | 11/1992 |
| EP | 0 546 697 | 6/1993 |
| EP | 994114 A2 | 4/2000 |
| GB | 1418822 | 12/1975 |
| GB | 2001638 | 2/1979 |
| JP | S42-17893 | 9/1967 |
| JP | S47-19261 | 6/1972 |
| JP | 01258658 | 10/1989 |
| JP | 4217893 | 8/1992 |
| JP | 2004051594 | 2/2004 |
| WO | WO-9308798 | 5/1993 |
| WO | WO-9309794 | 5/1993 |
| WO | WO-9428902 | 12/1994 |
| WO | WO-9616644 | 6/1996 |
| WO | WO-9810765 | 3/1998 |
| WO | WO-9938496 | 8/1999 |
| WO | WO-0048636 | 8/2000 |
| WO | WO-0121163 | 3/2001 |
| WO | WO-0121259 | 3/2001 |
| WO | WO-0140196 | 6/2001 |
| WO | WO-0141807 | 6/2001 |
| WO | WO-02/08228 | 1/2002 |
| WO | WO-02062322 | 8/2002 |
| WO | 02096435 A2 | 12/2002 |
| WO | 03/000343 | 1/2003 |
| WO | WO-03061638 | 7/2003 |
| WO | WO-03061648 | 7/2003 |
| WO | WO-2004012700 | 2/2004 |
| WO | WO-2004037262 | 5/2004 |
| WO | WO-2004043336 | 5/2004 |
| WO | WO-2004043464 | 5/2004 |
| WO | WO-2004/063172 | 7/2004 |
| WO | WO-2004064841 | 8/2004 |
| WO | WO-2005025570 | 3/2005 |
| WO | WO-2005048979 | 6/2005 |
| WO | WO-2005065639 | 7/2005 |
| WO | WO-2006017822 | 2/2006 |
| WO | 2008065444 A | 6/2008 |
| WO | WO 2010/005480 A2 | 1/2010 |
| WO | 2010/070318 A1 | 6/2010 |

OTHER PUBLICATIONS

Kienzle et al., "Die synthese von 2,3,4,5-1Htetrahydroimidazo-[2,1-b]chinazolin-2,5-dionen und analogen 2,3,4,5-1H-tetrahydroimidazo[1,2-a]thieno[2,3-d](bzw. [3,2-d])-pyrimidin-2,5-dionen," Helv. Chim. Acta, 1983, 66:148-157.

Martinez et al., "3,4-Dihydroquinolin-2(1H)-ones as combined inhibitors of thromboxane A2 synthase and cAMP phosphodiesterase." J. Med. Chem., 1992, 35:620-628.

Meanwell et al., "1,3-Dihydro-2H-imidazo[4,5-b]quinolin-2-ones—inhibitors of blood platelet cAMP phosphodiesterase and induced aggregation." J. Med. Chem., 1991, 34:2906-2916.

Meanwell et al., "Inhibitors of blood platelet cAMP phosphodiesterase. 2. Structure-activity relationships associated with 1,3-dihydro-2H-imidazo[4,5-b]quinolin-2-ones substituted with functionalized side chains." J. Med. Chem., 1992, 35: 2672-2687.

Stalder, "Metaboliten der 1,5-dihydroimidazo[2,1-b]chinazolin-2(3H)-one. Synthese und reaktionen einiger 1,5-dihydro-3-hydroxyimidazo[2,1-b]chinazolin-2(3H)-one," Helv. Chim. Acta, 1986, 69:1887-1897.

Venuti et al., "Inhibitors of cyclic AMP phosphodiesterase. 2. Structural variations of N-cyclohexyl-N-methyl-4-[(1,2,3,5-tetrahydro-2-oxoimidazo[2,1-b]quinazolin-7-yl)-oxy]butyramide (RS-82856)." J. Med. Chem., 1987, 30:303-318.

Venuti et al., "Inhibitors of cyclic AMP phosphodiesterase. 3. Synthesis and biological evaluation of pyrido and imidazolyl analogues of 1,2,3,5-tetrahydro-2-oxoimidazo[2,1-b]quinazoline." J. Med. Chem., 1988, 31:2136-2145.

Bell, Andrew S., et al. "7-Heteroaryl-1,2,3,5-tetrahydroimidazo[2,1-b]quinazolin-2(1H)-one Derivatives with Cardiac Stimulant Activity," Journal of Medicinal Chemistry, 1989, vol. 32, No. 9, pp. 2042-2049 (8 pages).

Kienzle, Frank, et al. "1,5-Dihydroimidazoquinazolinones as Blood Platelet Aggregation Inhibitors," European Journal of Medicinal Chemistry, 1982-17, No. 6, pp. 546-556 (10 pages).

Imidazo[2,1-b]quinazolin-2(3H)-one, 1,5-dihydro-3,3-dimethyl-,monohydrochloride (9Cl), as referenced in European Journal of Medicinal Chemistry (1982), 17(6), 547-56 (1 page).

Imidazo[2,1-b]quinazolin-2(3H)-one, 1,5-dihydro-3,3,6-trimethyl-, monohydrochloride (9Cl), as referenced in European Journal of Medicinal Chemistry (1982), 17(6), 547-56 (1 page).

Imidazo[2,1-b]quinazolin-2(3H)-one, 1,5-dihydro-3,3,6-trimethyl-, as supplied by Chemstep, France. Catalog Publication Date Jun. 19, 2007 (1 page).

Imidazo[2,1-b]quinazolin-2(3H)-one, 1,5-dihydro-3,3-dimethyl-, as supplied by Chemstep, France. Catalog Publication Date Jun. 19, 2007 (1 page).

Brown, L., et al., "Transdermal Delivery of Drugs," Annual Review of Medicine, 1988, pp. 221-229, vol. 39.

Kshirsagar, N.A., "Drug Delivery Systems," Indian Journal of Pharmacology, 2000, pp. S54-S61, vol. 32.

Tomer, A., "Effects of anagrelide on in vivo megakaryocyte proliferation and maturation in essential thrombocythemia," Blood, Mar. 2002, pp. 1602-1609, vol. 99.

Andes et al "Inhibition of platelet production induced by an antiplatelet drug, anagrelide, in normal volunteers," Thromb. Haemost., 1984, 52:325-8.

Agrylin (anagrelide hydrochloride), Product Monograph, Roberts Pharmaceutical Corp.; 1997.

Aldrich Catalogue 1996, p. 498.

"Blood," Journal of the American Society of Hematology; W. R. Saunders Company; vol. 94; No. 10; Supplement 1 (Part 1 of 2); Nov. 15, 1999; p. 701a.

Decision on FDA Citizen Petition No. 2004P-0365 by the FDA, Apr. 18, 2005.

A signed Declaration pursuant to 37 C.F.R. §1.132 by Dr. Richard Franklin submitted in U.S. Appl. No. 10/762,566 on Sep. 19, 2007 and Exhibit 1 to the Declaration (the curriculum vitae for Dr. Richard Franklin), 8 pgs.

FDA Citizen Petition No. 2004P-0365 on behalf of Shire US, Inc., Aug. 13, 2004.

Response to FDA Citizen Petition No. 2004P-0365 by Mylan Phermaceuticals, Inc., Sep. 8, 2004.

Response to FDA Citizen Petition No. 2004P-0365 by Barr Laboratories, Inc., Oct. 20, 2004.

Doherty, "Oral, Transdermal and Transurethral Therapies for Erectile Dysfunction" in Male Infertility and Dysfunction, Ch. 33, 1997.

Erusalimsky, Jorge et al, Is the platelet lowering activity of anagrelide mediated by its major metabolite 2-amino-5 6-dichloro-3,4-dihydroquinazoline (RL603)?, Experimental Hematology, 2002, vol. 30, No. 7, pp. 625-626.

Gaver et al, "Disposition of anagrelide, an inhibitor of platelet aggregation." Clin. Pharmacol. Ther., 1981, 29:381-386.

Green et al., "Management of the myeloproliferative disorders: distinguishing data from dogma," Hematol. J., 2004, 5 Suppl. 3:S126-S132.

Griesshammer, Martin et al. "Current treatment practice for essential thrombocythaemia in adults" Exp. Opin. Pharmacother., 2001, 2: 385-393.

International Search Report in connection with International Application No. PCT/CA2004/000096, dated Jun. 23, 2004.

International Search Report for PCT/US05/28086 mailed Jun. 14, 2006.

Jones et al., "Inhibitors of cyclic AMP phosphodiesterase. 1. Analogues of cilostamide and anagrelide," J. Med. Chem., 1987, 30:295-303.

Kelly et al., "Pharmacological treatment of heart failure," in Goodman and Gilman, Ch. 34, 1996.

Lane, William et al, "Anagrelide metabolite induces thrombocylopenia in mice by inhibitingmegakaryocyte maturation without inducing platelet aggregation," Experimental Hematology, 2001, vol. 29, No. 12, pp. 1417-1424.

Mazur et al "analysis of the mechanism of anagrelide-induced thrombocytopenia in humans" Blood, 1992, 79:1931-1937.

Morrison & Boyd, "Organic Chemistry," 3rd Ed. 1975, 344-347; 387-388.

Oertel, "Anagrelide, a selective thrombocytopenic agent." Am. J. Health Syst. Pharm., 1998, 55:1979-86.

Osinski, M., et al. "Inhibition of platelet-derived growth factor-induced mitogenesis by phosphodiesterase 3 inhibitors: Role of protein kinase A in vascular smooth muscle cell mitogenesis," Biochemical Pharmacology 2000, vol. 60, No. 3, pp. 381-387.

Pescatore, Scott et al. "Anagrelide: a novel agent for the treatment of myeloproliferative disorders," Exp. Opin. Pharmacother., 2000, 1: 537-546.

Petitt et al "Anagrelide for control of thrombocythemia in polycythemia and other myeloproliferative disorders." Semin. Hematol., 1997, 34:51-4.

Petrides, P., et al. "Anagrelide, a Novel Platelet Lowering Option in Essential Thrombocythaemia: Treatment Experience in 48 Patients in Germany," European Journal of Haematology, vol. 61, 1998, p. 71-76.

Solberg Jr, et al, "The effects of anagrelide on human megakaryocytopoiesis," British Journal of Haematology 1997, vol. 99, No. 1, pp. 174-180.

Spencer and Brogden, "anagrelide. A review of its pharmacodynamic and pharmacokinetic properties, and therapeutic potential in the treatment of thrombocythaemia." Drugs, 1994 47:809-22.

Storen, Elizabeth et al. "Long-term use of anagrelide in young patients with essential thrombocythemia," Blood, Feb. 15, 2001, vol. 97, No. 4, 863-866.

Tefferi, A., et al., "Spotlight Review—Classification and Diagnosis of myeloproliferative neoplasms: The 2008 World Health Organization criteria and point-of-care diagnostic algorithms," 2008 Nature Publishing Group. Table 1.

Trapp et al, "Anagrelide for treatment of patients with chronic myelogenous leukemia and a high platelet count." Blood Cells Mol. Dis., 1998, 24:9-13.

Citizen Petition, Arnall Golden Gregory LLP, Aug. 13, 2004, 159 pages.

Wagstaff, Antona J. et al., Anagrelide: A Review of its Use in the Management of Essential Thrombocythaemia, Drugs 2006, 66(1):111-131.

Wang, Guosu, et al., "Comparison of the Biological Activities of Anagrelide and its Major Metabolites in Haematopoietic Cell Cultures," British Journal of Pharmacology 2005, vol. 146:324-332.

West, A. R., "Solid State Chemistry and Its Applications," Wiley, New York, 1988, p. 358.

Wang et al., "Comparison of the Biological Activities of Anagrelide and its Major Metabolites in Haematopoietic Cell Cultures," British Journal of Pharmacology, vol. 146, 2005, pp. 324-332.

Barbui, T. et al., "Practice Guidelines for the Therapy of Essential Thrombocythemia," Feb. 2004, p. 215.

European Agency for the Evaluation of Medicinal Products (EMEA): Scientific Discussion of European Public Assessment Report (EPAR) Xagrid, 2004 http://www.emea.eu.int/humandocs/PDFs/EPAR/Xagrid/136504en6.pdf.

Shahin, R. et al., "Is the Platelet Lowering Activity of Anagrelide Mediated by its Major Metabolite 2-amino-5,6dichloro-3,4-dihydroquinazoline (RL603)? in Response," Experimental Hematology, vol. 30, No. 7, 2002, pp. 626-627.

Souhami, R. L. et al., "Textbook of Internal Medicine," Churchill-Livingstone, 1997, p. 1043, Table 25.53.

Ammar et al., "Design of a Transdermal Delivery System for Aspirin as an Antithrombotic Drug," International Journal of Pharmaceutics, vol. 327, 2006, pp. 81-88.

Solberg, "Therapeutic Options for Essential Thrombocythemia and Polycythemia Vera," Seminars in Oncology, vol. 28, Issue 3, Supplement 10, 2002, pp. 10-15.

Bonkovsky et al., "Drug-Induced Liver Injury," Zakim and Boyer's Hepatology, 5th Edition, 2006, p. 503.

Official Communication for U.S. Appl. No. 11/946,572 mailed Apr. 12, 2010.

Official Communication for U.S. Appl. No. 11/946,572 mailed Nov. 23, 2010.

Official Communication for U.S. Appl. No. 12/697,900 mailed Nov. 15, 2011.

Official Communication for U.S. Appl. No. 12/697,900 mailed May 8, 2012.

Binder, D. et al., "Thiophen als a strukturelement physiologisch aktiver substanzen, 8. mitt. 1H,5H-imidazo [1,2-a] thieno [3,4-d] pyrimidin-2(3H)-one (Thiophene as a structural element of physiologically active compounds, 8. 1H,5H-imidazo [1,2-a] thieno [3,4-d] pyrimidin-2(3H)-one.)" Arch. Pharm. (Weinheim) vol. 341, 1981, pp. 557-564.

Ishikawa, F. et al., "Cyclic Guanidines. 14. Imidazo[1,2-a]thienopyrimidin-2-one Derivatives as Blood Platelet Aggregation Inhibitors," J. Med. Chem. vol. 24, No. 4, 1981, pp. 376-382.

ISR Ref.; XP002543715 DATABASE STN Database Accession No. 1981:603987. 3-Alkylimidazothienopyrimidin-2-ones-JP1979-152466; accessed Sep. 1, 2009.

ISR Ref.; XP002543716 DATABASE STN Database Accession No. 1981-424964. Cyclic guanidines. XIII. Synthesis of 2-amino-4-phenyl-3,4-dihydrothieno[2,3-d]pyrimidine derivatives, Abstract and Chem. Pharm. Bull. vol. 28, No. 11, 1980, pp. 3172-3177.

ISR Ref.; XP002543717 DATABASE WPI Week 198227. 2,3-Di:hydro:imidazo:thieno:pyrimidine-2-one-show blood platelet agglutination inhibition using oral admin. Thomson Scientific, London AN 1982-55858E, 1982.

Grover, R. K. et al., "Base catalyzed intramolecular transamidation of 2-aminoquinazoline derivatives on solid phase," Tetrahedron, vol. 61, No. 21, 2005, pp. 5011-5018 ril.

Srivastava, G. K. et al., "Solid phase synthesis of 2-aminoquinazoline-based compounds," J. Comb. Chem. vol. 5, 2003, pp. 769-774.

ISR Ref.; XP002535240 Database Chemical Abstracts, Taibi, P. et al., "(Methoxycarbonylsulfamoyl) triethylammonium Hydroxide," Encyclopedia of Reagents for Organic Synthesis, John Wiley & Sons, Ltd., Chichester UK, 2001.

Chowdhury, A. Z. M. S. et al., "Synthesis of new heterocondensed pteridines," J. Heterocyclic Chem. vol. 38, No. 5, 2001, pp. 1173-1177.

Agrylin (anagrelide hydrochloride) Capsules, product monograph, Shire US Inc., NDA 20-333/S-010, 2003, pp. 3-12 11.

Lane, W. et al., "Anagrelide metabolite induces thrombocylopenia in mice by inhibition of megakaryocyte maturation without inducing platelet aggregation," Blood, vol. 94, 1999, 701a Supp. 1 (Part 1 of 2), Abstract #3097.

International Search Report and Written Opinion for International Patent Application No. PCT/GB2009/050508 mailed Jul. 29, 2009.

International Search Report and Written Opinion for International Patent Application No. PCT/GB2009/050509 mailed Sep. 11, 2009.

International Search Report and Written Opinion for International Patent Application No. PCT/GB2009/050510 mailed Jul. 21, 2009.

International Search Report and Written Opinion for International Patent Application No. PCT/GB2009/050511 mailed Oct. 16, 2009.

International Search Report and Written Opinion for International Patent Application No. PCT/GB2009/050512 mailed Jul. 28, 2009.

International Search Report and Written Opinion for International Patent Application No. PCT/GB2009/050513 mailed Jul. 1, 2009.

International Search Report and Written Opinion for International Patent Application No. PCT/GB2009/050514 mailed Jul. 20, 2009.

International Search Report and Written Opinion for International Patent Application No. PCT/GB2009/050515 mailed Aug. 20, 2009.

International Search Report and Written Opinion for International Patent Application No. PCT/GB2009/050516 mailed Jul. 29, 2009.

International Search Report and Written Opinion for International Patent Application No. PCT/GB2009/050517 mailed Nov. 3, 2009.

* cited by examiner

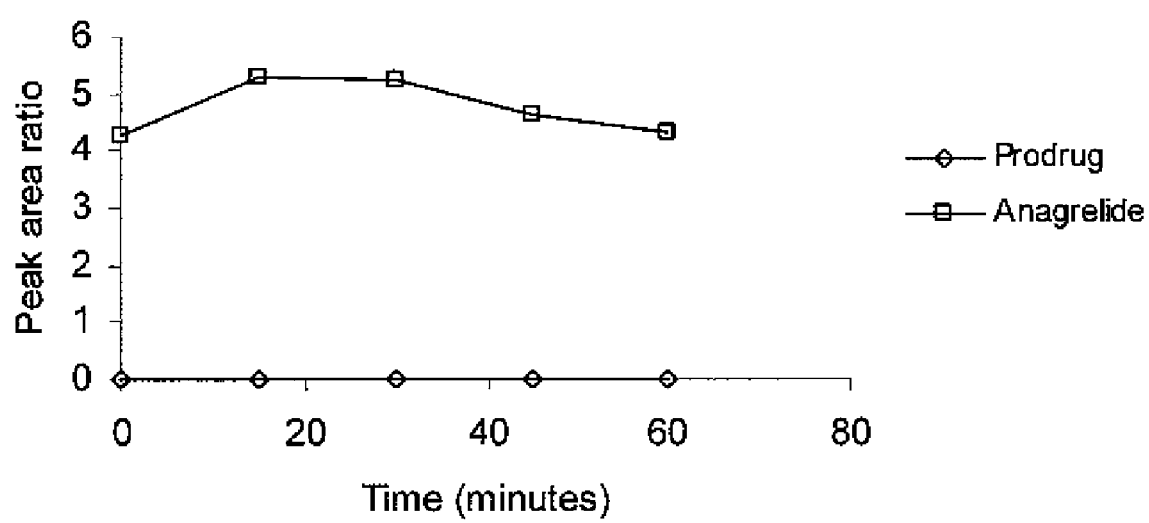

SUBSTITUTED QUINAZOLINES FOR REDUCING PLATELET COUNT

This application claims priority to U.S. Provisional Application Ser. No. 60/861,578 filed Nov. 28, 2006; the contents of which are incorporated by reference in their entirety.

FIELD OF THE INVENTION

This invention relates to the discovery of prodrugs of 3- or 5-substituted analogues of the selective platelet lowering agent anagrelide which have reduced potential for cardiovascular side-effects and which should therefore lead to improved patient compliance and safety in the treatment of myeloproliferative diseases. More specifically, the present invention relates to prodrugs of certain imidazoquinazoline derivatives which have utility as platelet lowering agents in humans. The compounds of the present invention function by inhibiting the formation of blood platelets.

BACKGROUND OF THE INVENTION

Anagrelide hydrochloride (Agrylin®, Xagrid®) is a novel orally administered imidazoquinazoline which selectively reduces platelet count in humans and is used for such purposes in the treatment of myeloproliferative diseases (MPDs), such as essential thrombocythemia (ET), where an elevated platelet count may put the patient at increased thrombotic risk. The chemical structure of anagrelide, 6,7-dichloro-1,5-dihydroimidazo[2,1-h]-quinazolin-2(3H)-one (hydrochloride monohydrate), is shown in the following formula:

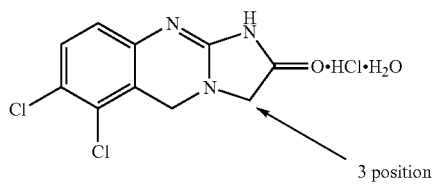

6,7-Dichloro-1,5-dihydroimidazo[2,1-b]-quinazolin-2(3H)-one hydrochloride monohydrate The principal side effects of anagrelide are cardiovascular in nature, tachycardia, palpitations etc and limit the utility of the drug. These are largely attributed to its metabolism to 3-hydroxyanagrelide. This compound was surprisingly found to be some 40-fold more potent as an inhibitor of PDEIII, and therefore potential inotropic agent, than anagrelide itself. Furthermore plasma exposure to this metabolite after treatment with anagrelide is typically three times greater than to the drug itself confirming its pivotal role. Consequently a series of 3-substituted anagrelide analogues has been investigated which has shown that it is possible to introduce metabolism blocking groups at that position and yet still retain the anti-megakaryocytic actions of the drug. Furthermore, these compounds have considerably less potential for cardiovascular effects than 3-hydroxyanagrelide. Indirect steric hindrance to the formation of the 3-hydroxy metabolite may also be achieved by substitution at the 5-position. The 3-substituted compounds typified, by the dimethyl or spiro-cyclopropyl analogues, are notably less soluble at physiological pH (~7) than the parent compound which presents a significant challenge to their efficient absorption.

Anagrelide HCl itself is a poorly soluble drug substance. In the pH range of 4-8, the solubility is less than 10 μg/mL. The solubility increases at pH values above and below this range; for example in 0.1M HCl the solubility is ~170 μg/mL and at pH 11.4 approaches 1 mg/mL. The dissociation constants (pKa1 and pKa2) of 2.9 and 9.8 were estimated from the solubility/pH profile of anagrelide HCl. Thus over much of the physiological pH range the drug has very poor aqueous solubility. Even material dissolving in the stomach at pH 1-2 may precipitate in the duodenum at pH 5-6. This presents potential problems for the quantitative absorption from the most likely site for absorption, namely the upper small intestine. As a consequence anagrelide is micronised prior to filling into capsules for clinical use to ensure maximal absorption. This and anagrelide's inherent potency as an anti-megakaryocytic agent—in vitro $IC_{50}$~27 nM and in vivo doses of just 1-2 mg—serve to limit the potential problem of incomplete absorption. Indeed, a radiolabelling study in humans showed that following the oral administration of 1 mg $^{14}C$-labelled drug >75% of the administered radioactivity was recovered in the urine implying that at least after this dose absorption was >75%. However for those patients requiring larger doses either as the result of relative insensitivity to the drug, higher first-pass pre-systemic metabolism or greater body weight, the possibility exists for incomplete absorption. This would be expected to lead to increased variability in attained plasma drug concentrations and consequential variability in patient response.

Furthermore for less potent analogues of anagrelide, even though they may have better cardiovascular profiles, problems of incomplete absorption may be encountered. Improved water solubility though the use appropriate open ring pro-drugs of anagrelide may therefore offer significant advantage in minimizing this risk.

WO2004/063172 relates to the use of 2-amino-2H-quinazoline derivatives for producing therapeutic agents for the treatment of myeloproliferative diseases, high blood pressure and bronchodilation.

SUMMARY OF THE INVENTION

This invention provides for prodrugs of anagrelide derivatives substituted at either the 3- or 5-position. In these anagrelide derivatives, metabolism to an analogue of the cardioactive 3-hydroxyanagrelide is blocked either directly (3-substitution) or indirectly (5-substitution). The prodrugs are notably more soluble in vitro (and under anticipated in vivo conditions) than their ring closed analogues offering the potential for better absorption from the GI tract. Such compounds would spontaneously and completely ring close at pH 7 or above thus offering a convenient means of delivering these ring closed anti-megakaryocytic (platelet lowering) agents to the systemic circulation. Since the preferred site of metabolism of anagrelide is the 3-position, such compounds are likely to present improved pharmacokinetic profile and hence improve patient compliance and convenience enabling a broader spectrum of patients to be effectively treated. In the case of the 5-substituted compounds it is expected that a bulky group is more effective than a smaller group when cyclised to the 'closed ring' anagrelide analogue. Groups such as t-butyl and other bulky blocking groups are thus expected to be of most utility when substituted at the 5-position. A substituent comprising a large group at the 5-position is expected to sterically hinder access to the 3-position by the metabolising cytochrome's active site. This should inhibit formation of the cardioactive metabolite, 3-hydroxyanagrelide.

The ring closed compounds of the present invention are especially beneficial because surprisingly they have dramatically lower PDE III inhibitory activity (and hence lower cardioactive potential) than the active metabolite of anagrelide, 3-hydroxyanagrelide and yet also surprisingly retain their anti-megakaryocytic activity. Indeed these compounds have therapeutic indices which are much more favourable than that for anagrelide itself.

In one embodiment, the present invention comprises a prodrug of an anagrelide analogue comprising a 3-, 5-, 3,3- or 5,5-substituted anagrelide compound. Thus, for example, in the 3-substituted derivatives, first pass metabolism (of the rapidly ring closed analogue) to 3-hydroxyanagrelide is directly blocked. In particular, the invention relates to prodrugs of an anagrelide analogue wherein first pass metabolism to the corresponding analogue of 3-hydroxyanagrelide is effectively blocked.

According to the present invention, there is provided a compound of Formula (I) or a pharmaceutically acceptable salt or solvate thereof

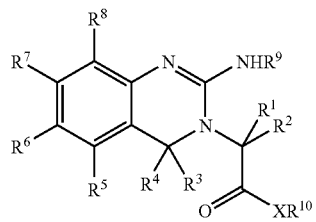

(1)

wherein:
$R^1$, $R^2$, $R^3$ and $R^4$ independently represent hydrogen or a blocking group which functions to prevent metabolic reaction either directly or indirectly at the 3-position;
or $R^1$ and $R^2$, and/or $R^3$ and $R^4$ together with the carbon to which they are attached form a blocking group which functions to prevent metabolic reaction either directly or indirectly at the 3- or 5-position of substitution, the remainder of groups $R^1$ to $R^4$ being hydrogen;
$R^5$ is selected from the group comprising: fluoro, chloro, bromo and iodo;
$R^6$ is selected from the group comprising: fluoro, chloro, bromo and iodo; and
$R^7$ and $R^8$ are independently selected from the group comprising: H; halo; cyano; $C_{1-6}$ alkyl, $C_{1-6}$ haloalkyl, $C_{1-6}$ alkoxy, and $C_{1-6}$ haloalkoxy; and
$R^9$ is H or $C_{1-6}$alkyl,
$R^{10}$ is selected from the group comprising: hydrogen; $C_{1-6}$ alkyl, $C_{2-6}$ alkenyl, $C_{2-6}$ alkynyl and $C_{3-8}$ cycloalkyl wherein each of the foregoing groups may be optionally substituted by 1 to 5 groups chosen independently from the group comprising: halo, hydroxyl, cyano, nitro, $C_{1-4}$ alkylsulphonyl and COOH; or $R^{10}$ is a pharmaceutically acceptable cation, and
X is O or S,
provided always that $R^1$, $R^2$, $R^3$ and $R^4$ are not all hydrogen.

In an embodiment when one of $R^1$ and $R^2$ is methyl and $R^3$ and $R^4$ are hydrogen then other of $R^1$ and $R^2$ is not hydrogen.

In one embodiment:
$R^1$ and $R^2$, are independently selected from the group comprising: H; halo; cyano; $C_{1-6}$ alkyl, $C_{2-6}$ alkenyl, $C_{2-6}$ alkynyl, $C_{3-8}$ cycloalkyl wherein said alkyl, alkenyl, alkynyl or cycloalkyl groups may be optionally substituted by 1 to 5 groups chosen independently from the group comprising: halo, hydroxyl, cyano, nitro, $C_{1-4}$ alkylsulphonyl and COOH; $C_{1-6}$ hydroxyalkyl; $C_{1-6}$ carboxyalkyl; and sulphide;

or $R^1$ and $R^2$ together with the carbon to which they are attached form a $C_{3-8}$ carbocyclic ring may be optionally substituted by 1 to 5 groups chosen independently from the group comprising: halo, hydroxyl, cyano, nitro, $C_{1-4}$ haloalkyl, $C_{1-4}$ alkylsulphonyl and COOH;
or $R^1$ and $R^2$ together with the carbon to which they are attached represent a $C_{2-6}$ alkenyl or $C_{2-6}$ alkynyl group bound through a double bond to the ring to which it is attached and being optionally substituted by one to three groups independently selected from the group comprising: halo, hydroxyl, cyano, $C_{1-4}$ haloalkyl and COOH, provided always that one of $R^1$ and $R^2$ is not hydroxyl when the other is methyl.

In a preferred set of compounds, $R^1$ is an optionally substituted $C_{1-4}$ alkyl or $C_{3-8}$ cycloalkyl group.

In a preferred set of compounds, $R^2$ is an optionally substituted $C_{1-4}$ alkyl or $C_{3-8}$ cycloalkyl group.

Other preferred compounds are those in which at least one of $R^1$ and $R^2$ is $-C(H)_n(F)_m$ or $-C(H)_n(F)_m-C(H)_p(F)_q$, where m=2 or 3, and n=(3−m); and p=2 or 3, and q=(3−p).

More preferably at least one of $R^1$ and $R^2$ is $CF_3$ or $CHF_2$. Most preferably, at least one of $R^1$ and $R^2$ is $CF_3$.

In an embodiment, $R^1$ is preferably methyl, cyclopropyl, $CF_3$ or $CHF_2$. Most preferably, $R^1$ is methyl.

In an embodiment, $R^2$ is preferably methyl, cyclopropyl, $CF_3$ or $CHF_2$. Most preferably $R^2$ is methyl.

In another preferred set of compounds, $R^1$ and $R^2$ together form an optionally substituted $C_{3-8}$ cycloalkyl group. Most preferably this is a cyclopropyl group.

In an embodiment:
$R^3$ and $R^4$ are independently selected from the group comprising: H; halo; cyano; $C_{1-6}$ alkyl, $C_{2-6}$ alkenyl, $C_{2-6}$ alkynyl, $C_{3-8}$ cycloalkyl wherein said alkyl, alkenyl, alkynyl or cycloalkyl groups may be optionally substituted by 1 to 5 groups chosen independently from the group comprising: halo, hydroxyl, cyano, nitro, $C_{1-4}$ alkylsulphonyl and COOH; $C_{1-6}$ hydroxyalkyl; $C_{1-6}$ carboxyalkyl; and sulphide;
or $R^3$ and $R^4$ together with the carbon to which they are attached form a $C_{3-8}$ carbocyclic ring may be optionally substituted by 1 to 5 groups chosen independently from the group comprising: halo, hydroxyl, cyano, nitro, $C_{1-4}$ haloalkyl, $C_{1-14}$ alkylsulphonyl and COOH;
or $R^3$ and $R^4$ together represent a $C_{2-6}$ alkenyl or $C_{2-6}$ alkynyl group bound through a double bond to the ring to which it is attached and being optionally substituted by one to three groups independently selected from the group comprising: halo, hydroxyl, cyano, $C_{1-4}$ haloalkyl and COOH.

In an embodiment, $R^3$ is H or $C_{1-6}$ alkyl. Preferably, $R^3$ is H.
In an embodiment, $R^4$ is H or $C_{1-6}$ alkyl. Preferably, $R^4$ is H.
In an embodiment, $R^5$ is chloro.
In an embodiment, $R^6$ is chloro.
In an embodiment, $R^7$ is H.
In an embodiment, $R^8$ is H.
In an embodiment, $R^9$ is H or Me. In one embodiment, $R^9$ is H and compounds in which $R^9$ is H enjoy good solubility. When $R^9$ is a $C_{1-6}$ alkyl group, such as Me, the PDE III inhibiting activity is effectively eliminated. Me represents a particularly preferred alkyl substituent.

In an embodiment, $R^{10}$ is H or optionally substituted $C_{1-6}$ alkyl. Most preferably, $R^{10}$ is $C_{1-6}$ alkyl. In an alternative embodiment, $R^{10}$ is Na or K, with Na being preferred.

In an embodiment, X is O.
In a further embodiment,
$R^1$ and $R^2$ are independently selected from the group comprising: H; cyano; $C_{1-6}$ alkyl, $C_{2-6}$ alkenyl, $C_{2-6}$ alkynyl, $C_{3-8}$ cycloalkyl wherein said alkyl, alkenyl alkynyl or cycloalkyl groups may be optionally substituted by 1 to 5 groups chosen independently from the group comprising:

halo, hydroxyl, cyano, nitro, $C_{1-4}$ alkylsulphonyl and COOH; $C_{1-6}$ hydroxyalkyl; $C_{1-6}$ carboxyalkyl; and sulphide;

or $R^1$ and $R^2$ together with the carbon to which they are attached form a $C_{3-8}$ carbocyclic ring may be optionally substituted by 1 to 5 groups chosen independently from the group comprising: halo, hydroxyl, cyano, nitro, $C_{1-4}$ haloalkyl, $C_{1-4}$ alkylsulphonyl and COOH;

or $R^1$ and $R^2$ together represent a $C_{2-6}$ alkenyl or $C_{2-6}$ alkynyl group bound through a double bond to the ring to which it is attached and being optionally substituted by one to three groups independently selected from the group comprising: halo, hydroxyl, cyano, $C_{1-4}$ haloalkyl and COOH;

$R^3$ and $R^4$ are hydrogen;

$R^5$ is selected from the group comprising: fluoro, chloro, bromo and iodo;

$R^6$ is selected from the group comprising: fluoro, chloro, bromo and iodo; and $R^7$, $R^8$, $R^9$ and $R^{10}$ are hydrogen.

Another preferred group of compounds is those in which neither $R^1$ nor $R^2$ is hydrogen. Amongst these, it is preferred when $R^1$ and 2 are both independently selected from the group comprising: cyano, $C_{1-6}$ alkyl, $C_{2-6}$ alkenyl, $C_{2-6}$ alkynyl, in which the alkyl, alkenyl, and alkynyl groups may be optionally substituted;

or wherein $R_1$ and $R_2$ together with the carbon to which they are attached form an optionally substituted $C_{3-8}$ carbocyclic ring or wherein $R_1$ and $R_2$ together represent an optionally substituted $C_{2-6}$ alkenyl or $C_{2-6}$ alkynyl group.

Particularly preferred individual compounds of the invention include:

The 3-methylanagrelide derivative

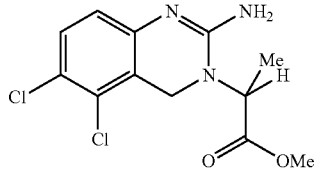

3,3-dimethylanagrelide derivative

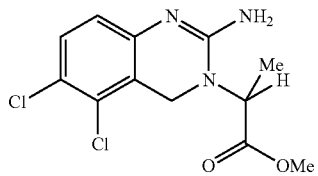

and the corresponding spiro 3-cyclopropyl derivative

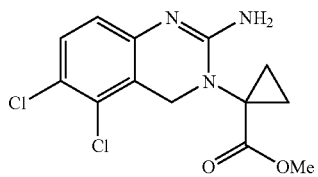

Regarding the use of the compounds of the invention in humans, there is provided:

a pharmaceutical composition comprising a compound of formula (I), or a pharmaceutically acceptable salt or solvate thereof, together with a pharmaceutically acceptable diluent or carrier, which may be adapted for oral, parenteral or topical administration;

a compound of formula (I), or a pharmaceutically acceptable salt or solvate thereof, or a pharmaceutical composition containing any of the foregoing, for use as a medicament;

the use of a compound of formula (I), or a pharmaceutically acceptable salt or solvate thereof in the manufacture of a medicament for the treatment of a disease selected from: myeloprolific diseases and generalised thrombotic diseases.

a method of treating a disease selected from: myeloprolific diseases and generalised thrombotic diseases in a human, which comprises treating said human with an effective amount of a compound of formula (I), or a pharmaceutically acceptable salt or solvate thereof, or with a pharmaceutical composition containing any of the foregoing.

The present invention also encompasses a method of treating a patient having essential thrombocythemia or other myelproliferative disease or thrombotic cardiovascular disease or high blood platelet count, which method comprises administering to the patient a therapeutically effective amount of a compound of the present invention.

Another embodiment of the present invention includes a method of reducing blood platelet count within a patient, which method comprises administering to the patient a therapeutically effective amount of a compound of the present invention.

The present invention encompasses providing the compounds of the present invention for the methods listed above, among others, wherein cardiotoxicity is reduced compared to using anagrelide.

The present invention also encompasses pharmaceutical compositions comprising a compound or pharmaceutically acceptable salt of a compound of the present invention and a pharmaceutically acceptable carrier.

Pharmaceutically acceptable salts of the compounds of Formula (I) include acid addition salts. Examples include hydrochloric and hydrobromide salts.

BRIEF DESCRIPTION OF THE DRAWINGS

FIG. 1 shows the levels of anagrelide prodrug, ethyl-5,6-dichloro-3,4-dihydro-2-(1H)-iminoquinazoline-3 acetate and anagrelide observed in samples of human plasma, incubated at room temperature over one hour.

DETAILED DESCRIPTION OF THE INVENTION

The present invention is directed to new prodrugs of 3- or 5-substituted analogues of the established platelet lowering agent anagrelide. These compounds spontaneously ring close at pH's 7 and above to yield 3- or 5-substituted anagrelides that retain the anti-megakaryocytic properties (hence platelet lowering activity) of anagrelide but have reduced PDEIII inhibitory properties and hence lower potential for unwanted cardiovascular and anti-aggregatory side-effects.

Appropriate substitution at the 3-position of the anagrelide molecule effectively blocks the principal site of metabolism and thus precludes the formation of the highly potent PDEIII inhibitor 3-OH anagrelide. The 5-substituted analogues have the potential to indirectly sterically hinder metabolism at the preferred 3-position. These 3- or 5-substituted analogues of anagrelide also have the potential for improved pharmacokinetic characteristics since the 3-position in the anagrelide molecule is known to be the major site of metabolism which is the principal mechanism of drug clearance.

Use of the corresponding "open ring" prodrugs of these 3- or 5-substituted analogues could offer the added value of improved rates of dissolution and water solubility, allowing easier formulation. For example the aqueous solubility of anagrelide at pH 7 is <10 ug/ml. For ethyl-5,6-dichloro-3,4-dihydro-2-(1H)-iminoquinazoline-3-acetate HBr—an unsubstituted but representative example of these ring open prodrugs—the solubility is ~5.5 mg/ml in distilled water.

Such prodrugs are likely to be extremely rapidly and completely cyclised in plasma to the closed ring 3-alkylanagrelide analogues. For example the rapid and quantitative conversion of ethyl-5,6-dichloro-3,4-dihydro-2-(1H)-iminoquinazoline-3-acetate HBr—an unsubstituted but representative example of these ring open prodrugs—to anagrelide was demonstrated in human plasma using LC/MS-MS analytical techniques. Human plasma was spiked with anagrelide prodrug (final concentration 100 ng/mL). Immediately after mixing, and at 15, 30, 45 and 60 minutes afterward samples were analysed for anagrelide prodrug and anagrelide. Even at the first point of measurement no prodrug could be found demonstrating the rapid and complete conversion to anagrelide itself. FIG. 1 shows the levels of anagrelide prodrug, ethyl-5,6-dichloro-3,4-dihydro-2-(1H)-iminoquinazoline-3 acetate and anagrelide observed in samples of human plasma, incubated at room temperature over one hour.

The potential benefit of improved water solubility on the absorption of these open-ring analogues was shown in a comparative bioavailability study in the dog. Using the unsubstituted ethyl-5,6-dichloro-3,4-dihydro-2-(1H)-iminoquinazoline-3-acetate HBr as a model compound, a comparison was made of the systemic availability of anagrelide when given as this compound or as anagrelide itself in equimolar doses (7.7 & 6.1 mg/kg respectively). Examination of pharmacokinetic parameters for the prodrug showed an approximately 17-fold higher $C_{max}$, and a mean 16-fold higher AUC for anagrelide than when the drug itself was administered.

These results implied that the inherent absorption of anagrelide at this dose (6.1 mg/kg, albeit 200 fold above the clinical dose) was comparatively poor (<6.25%) since there was little evidence for marked changes in metabolism, the likely alternative explanation. The metabolite-to-drug exposure ratio after anagrelide was 1.5 compared to 0.9 after the prodrug.

This study (see tables below) also showed that there was also considerably less variability in $C_{max}$ and AUC after the prodrug. For example $C_{max}$ for anagrelide after the prodrug ranged from 170-418 ngmL$^{-1}$ (relative standard deviation, RSD, 26%) compared to 9.5 to 44.3 ngmL$^{-1}$ after anagrelide itself (RSD 62.5%). Similarly the AUC for anagrelide after the prodrug ranged from 367 to 1470 ng.hmL$^{-1}$ (RSD 34%) compared to 21.6 to 188 ng.hmL$^{-1}$ (RSD 71%) after anagrelide itself. The lesser variability was consistent with more efficient absorption. This study illustrated the potential benefits of the open-ring prodrugs to improve absorption.

TABLE 1

Pharmacokinetic parameters of anagrelide following a single oral (capsule) administration of anagrelide or an ester open ring prodrug of anagrelide to male dogs at equivalent molar doses

| Dog ID number | $C_{max}$ (ng/mL) | $T_{max}$ (hours) | $AUC_{0-t}$ (ng · h/mL) | $AUC_{infin}$ (ng · h/mL) | k (hours$^{-1}$) | t½ (hours) |
|---|---|---|---|---|---|---|
| Anagrelide (6.1 mg/kg) | | | | | | |
| 1 | 15.7 | 16 | 141 | — | [e] | — |
| 3 | 14.8 | 1.5 | 42.0 | 42.3[c] | 0.4459[c] | 1.6[c] |
| 11 | 25.0 | 2 | 188 | 193[c] | 0.3119[c] | 2.2[c] |
| 23 | 9.50 | 1.5 | 21.6 | 23.1[d] | 0.1953[d] | 3.5[d] |
| 29 | 44.3 | 1 | 88.9 | 89.3 | 0.3031 | 2.3 |
| Mean | 21.9 | 1.5[b] | 96.3 | — | — | — |
| SD | 13.7 | | 68.9 | — | — | |
| Ester prodrug of anagrelide (7.5 mg/kg) | | | | | | |
| 1 | 213 | 3 | 678 | 679 | 0.1969 | 3.5 |
| 3[a] | 170 | 1 | 367 | 369 | 0.3071 | 2.3 |
| 11 | 418 | 4 | 1440 | 1440[d] | 0.1789[d] | 3.9[d] |
| 23 | 334 | 3 | 951 | 952 | 0.4941 | 1.4 |
| 29 | 353 | 6 | 1470 | 1470 | 0.4857 | 1.4 |
| Mean | 330 | 3.5[b] | 1130 | 1030 | 0.3922 | 1.8[f] |
| SD | 86 | | 390 | 400 | 0.1692 | |

[a]Animal vomited ca 1 hour post-dose, excluded from calculation of mean
[b]Median
[c]Estimate based on two data points only, therefore did not meet acceptance criteria, excluded from calculation of mean
[d]Could not be estimated in accordance with all acceptance criteria, excluded from calculation of mean
[e]Could not be estimated from the available data
[f]Calculated as ln2/(mean rate constant)

TABLE 2

Pharmacokinetic parameters of 3-hydroxy anagrelide, following a single oral (capsule) administration of anagrelide or an ester prodrug of anagrelide to male dogs at equivalent molar doses

| Dog ID number | $C_{max}$ (ng/mL) | $T_{max}$ (hours) | $AUC_{0-t}$ (ng · h/mL) | $AUC_{infin}$ (ng · h/mL) | k (hours$^{-1}$) | t½ (hours) |
|---|---|---|---|---|---|---|
| Anagrelide (6.1 mg/kg) | | | | | | |
| 1 | 14.1 | 16 | 131 | — | [d] | — |
| 3 | 18.0 | 1.5 | 64.6 | 65.0 | 0.2854 | 2.4 |
| 11 | 29.9 | 16 | 274 | — | [d] | — |
| 23 | 19.4 | 1.5 | 50.7 | 51.8 | 0.2314 | 3.0 |
| 29 | 43.0 | 1.5 | 122 | 123 | 0.2966 | 2.3 |
| Mean | 24.9 | 1.5[b] | 128 | 79.9 | 0.2711 | 2.6[e] |
| SD | 11.7 | | 89 | 37.9 | 0.0349 | |
| Ester prodrug of anagrelide (7.5 mg/kg) | | | | | | |
| 1 | 185 | 3 | 564 | 566 | 0.1569 | 4.4 |
| 3[a] | 106 | 1.5 | 303 | 303 | 0.2510 | 2.8 |
| 11 | 347 | 4 | 1280 | 1290[c] | 0.1235[c] | 5.6[c] |
| 23 | 269 | 3 | 876 | 878 | 0.4425 | 1.6 |
| 29 | 241 | 6 | 1240 | 1240 | 0.3776 | 1.8 |
| Mean | 261 | 3.5[b] | 990 | 895 | 0.3257 | 2.1[e] |
| SD | 67 | | 337 | 337 | 0.1497 | |

[a]Animal vomited ca 1 hour post-dose, excluded from calculation of mean
[b]Median
[c]Could not be estimated in accordance with all acceptance criteria (excluded from calculation of mean
[d]Could not be estimated from the available data
[e]Calculated as ln2/(mean rate constant)

For those 3- or 5-substituted anagrelide analogues which have a lower therapeutic potency (but not inherent activity) than anagrelide itself, a potentially higher absolute dose may be needed which could present problems for absorption. For example 3, 3, dimethyl anagrelide (anti-megakaryocytic IC$_{50}$ ~160 nM cf 27 nM for anagrelide) may need to be given at 6 times the current clinical dose of anagrelide. In this situation absorption may be less than complete and a prodrug may be needed to ensure efficient absorption from the GI tract.

The compounds of Formula I can be prepared in an analogous manner to those described in U.S. Pat. Nos. 4,256,748 and 6,388,073. The disclosures of the synthetic procedures used in each of these documents is intended specifically to be incorporated into this disclosure and forms part of the disclosure of this invention. The contents are not presented here in full for the purposes of brevity but the skilled person is specifically directed to these documents.

A person skilled in the art will be aware of variations of, and alternatives to, the processes referred to in U.S. Pat. No. 4,256,748 which allow the individual compounds defined by formula (I) to be obtained having been now revealed as desirable targets. The present invention thus further encompasses methods of manufacturing a compound of the present invention to the extent that such processes produce novel intermediates and/or employ novel process features.

It will also be appreciated by a person skilled in the art that the compounds of the invention could be made by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions), "March's Advanced Organic Chemistry—Reactions, Mechanisms and Structure", M B Smith, J. March, Wiley, (5th edition or later) "Advanced Organic Chemistry, Part B, Reactions and Synthesis", F A Carey, R J Sundberg, Kluwer Academic/Plenum Publications, (2001 or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" R K Mackie and D M Smith (Longman) (1982 or later editions), etc., and the references therein as a guide.

It will also be apparent to a person skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein.

Definitions

Halo means a group selected from: fluoro, chloro, bromo or iodo.

The term "alkyl" as used herein as a group or a part of a group refers to a straight or branched hydrocarbon chain containing the specified number of carbon atoms. For example, $C_{1-10}$ alkyl means a straight or branched alkyl containing at least 1 and at most 10 carbon atoms. Examples of "alkyl" as used herein include, but are not limited to, methyl, ethyl, n-propyl, n-butyl, n-pentyl, isobutyl, isopropyl, t-butyl, hexyl, heptyl, octyl, nonyl and decyl. A $C_{1-4}$ alkyl group is one embodiment, for example methyl, ethyl, n-propyl, isopropyl, n-butyl, isobutyl or t-butyl.

The term "cycloalkyl" as used herein refers to a non-aromatic monocyclic hydrocarbon ring of 3 to 8 carbon atoms such as, for example, but not limited to, cyclopropyl, cyclobutyl, cyclopentyl, cyclohexyl or cycloheptyl.

The term "spirocyclic" as used herein refers to a ring system joined to a second ring system at one carbon atom.

The term "alkoxy" as used herein refers to a straight or branched hydrocarbon chain group containing oxygen and the specified number of carbon atoms. For example, $C_{1-6}$ alkoxy means a straight or branched alkoxy containing at least 1 and at most 6 carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. A $C_{1-4}$ alkoxy group is one embodiment, for example methoxy, ethoxy, propoxy, prop-2-oxy, butoxy, but-2-oxy or 2-methylprop-2-oxy.

The term "hydroxyalkyl" as used herein as a group refers to a straight or branched hydrocarbon chain containing the specified number of carbon atoms, which is substituted by 1-3 hydroxyl groups. For example, $C_{1-4}$ hydroxyalkyl means a straight or branched alkyl chain containing from 1 to 4 carbon atoms and at least one hydroxyl group; examples of such group include hydroxymethyl, hydroxyethyl, hydroxypropyl, hydroxyisopropyl, hydroxybutyl and the like.

The term "alkenyl" as used herein as a group or a part of a group refers to a straight or branched hydrocarbon chain containing the specified number of carbon atoms and containing at least one double bond. For example, the term "$C_{2-6}$ alkenyl" means a straight or branched alkenyl containing at least 2 and at most 6 carbon atoms and containing at least one double bond. Examples of "alkenyl" as used herein include, but are not limited to, ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl. It will be appreciated that in groups of the form —O—$C_{2-6}$ alkenyl, the double bond is preferably not adjacent to the oxygen.

The term "alkynyl" as used herein as a group or a part of a group refers to a straight or branched hydrocarbon chain containing the specified number of carbon atoms and containing at least one triple bond. For example, the term "$C_{2-6}$ alkynyl" means a straight or branched alkynyl containing at least 2 and at most 6 carbon atoms and containing at least one triple bond. Examples of "alkynyl" as used herein include, but are not limited to, ethynyl, 2-propynyl, 3-butynyl, 2-butynyl, 2-pentynyl, 3-pentynyl, 3-methyl-2-butynyl, 3-methylbut-2-ynyl, 3-hexynyl and 1,1-dimethylbut-2-ynyl. It will be appreciated that in groups of the form —O—$C_{2-6}$ alkynyl, the triple bond is preferably not adjacent to the oxygen. The term "halo" refers to halogens such as fluorine, chlorine, bromine or iodine atoms.

The term "sulfide" refers to a radical of $R_a$—S—$R_b$, wherein a sulfur atom is covalently attached to two hydrocarbon chains, $R_a$ and $R_b$, wherein the two hydrocarbon chains may be, for example, but not limited to, any discussed above.

The compounds of the invention, i.e. those of formula (I), when cyclised may possess antimegakaryocytic activity in humans. Such activity may be assessed using a well established model. Assessment of the in vitro anti-megakaryocytic activity—and potentially therefore the platelet lowering capability—of the anagrelide prodrugs can be determined using the model of megakaryocytopoiesis (Cohen-Solal et al., Thromb. Haemost. 1997, 78:37-41 and Cramer et al, Blood, 1997, 89:2336-46). This involves examining the differentiation of human CD34$^+$ stem cells into megakaryocytes which ultimately give rise to blood platelets.

The compounds of the invention may be particularly useful in the treatment of myeloproliferative diseases. The compounds may also find utility in the treatment of generalised thrombotic diseases.

It is to be appreciated that references to treatment include prophylaxis as well as the alleviation and/or cure of established symptoms of a condition. "Treating" or "treatment" of a state, disorder or condition includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

Myeloproliferative diseases which may be treatable with the compounds of the present invention include: essential thrombocythemia, polycythema vera, chronic idiopathic myelofibrosis, chronic myeloid leukaemia with residual thrombocytosis, reactive thrombocytosis immediately preceding a surgical procedures, as an immediate or post operative preventative measures to minimise the risk of thrombus formation during or post surgery.

Thrombotic cardiovascular diseases (TCVD) (i.e. patients at increased generalised thrombotic risk) which may be treatable with the compounds of the present invention include: myocardial infarct (heart attack) thrombotic stroke, patients having undergone coronary stent placement.

The compounds of the present invention may also find utility in indicated for the reduction of atherothrombotic events as follows: recent MI, recent stroke or established peripheral arterial disease, acute coronary syndrome (unstable angina/non-Qwave MI), cardiovascular death, MI, stroke, and refractory ischemia.

EXAMPLE 1

The spirocyclopropylanagrelide derivative can be prepared using established chemistry as described previously according to the following reaction scheme. Other derivatives can be made in a likewise manner. The final product is obtained by cyclisation of the cyclopropyl precursor in the presence of cyanogen bromide and ethanol.

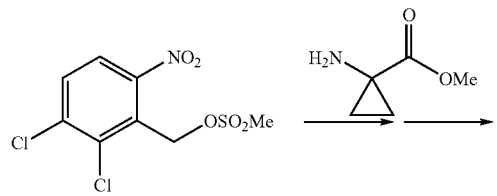

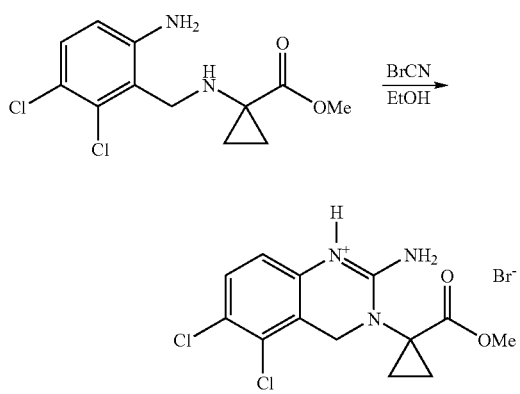

EXAMPLE 2

The solubilities of various salts was investigated in three solvents [distilled water (pH 5.0), 50 mM ammonium formate (pH 7.9) and 0.1 M hydrochloric acid (pH0.6)]. An excess of the salt was suspended in the chosen medium and sonicated for 3 minutes. The mixture was centrifuged for 10 minutes, the supernatant liquid was collected and the solubility was measured. Table 3 shows the results of the measurements.

| Solubilities of 2,2-Disubstituted 2-(2-Amino-5,6-dichloro-4H-quinazolin-3-yl)-propionates ($\mu$g mL$^{-1}$ at ca. 20° C.) | | | |
|---|---|---|---|
| Compound | Ammonium formate (50 mM, pH 7.9) | Water (pH 5.0) | Hydrochloric acid (0.1M, pH 0.6) |
| *(structure 1)* | 4 | 20 | 215 |
| *(structure 2)* | 16 | 7340 | 46 |
| *(structure 3)* | 1 | 2 | 35 |
| *(structure 4)* | unstable | 7060 | 6430 |

-continued

Solubilities of 2,2-Disubstituted 2-(2-Amino-5,6-dichloro-4H-quinazolin-3-yl)-propionates
(μg mL$^{-1}$ at ca. 20° C.)

| Compound | Ammonium formate (50 mM, pH 7.9) | Water (pH 5.0) | Hydrochloric acid (0.1M, pH 0.6) |
|---|---|---|---|
|  | 11 | 10 | 169 |

The figures show that the compounds of the invention have substantially improved solubility over their corresponding closed ring counterparts. This means that the compounds can be formulated and administered to patients in higher dosages than is possible for the closed ring versions. This represents a major clinical advantage.

The invention claimed is:

1. A platelet lowering compound of Formula (II):

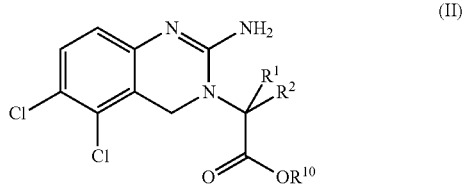

or a pharmaceutically acceptable salt thereof, wherein $R^1$ and $R^2$ are an independently selected $C_{1-6}$ alkyl and $R^{10}$ is a $C_{1-6}$ alkyl, and wherein the compound of formula (II) cyclizes spontaneously at pH 7 or above.

2. A compound as claimed in claim 1, wherein $R^1$ is a $C_{1-4}$ alkyl.

3. A compound as claimed in claim 1, wherein $R^2$ is a $C_{1-4}$ alkyl.

4. A compound as claimed in claim 1, wherein $R^1$ is methyl.

5. A compound as claimed in claim 1, wherein $R^2$ is methyl.

6. A compound as claimed in claim 1, wherein $R^1$, $R^2$, and $R^{10}$ are each a methyl group.

7. A pharmaceutical composition comprising a compound of formula (II) as defined in claim 1, or a pharmaceutically acceptable salt thereof, together with a pharmaceutically acceptable diluent or carrier.

8. A compound of Formula (III):

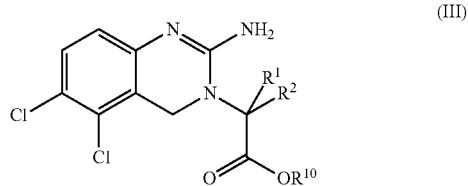

or a pharmaceutically acceptable salt thereof, wherein $R^1$ and $R^2$ together form a $C_{3-8}$ cycloalkyl group and $R^{10}$ is a $C_{1-6}$ alkyl.

9. A compound as claimed in claim 8, wherein $R^1$ and $R^2$ together form a cyclopropyl group.

10. A pharmaceutical composition comprising a compound of formula (III), as defined in claim 8, or a pharmaceutically acceptable salt thereof, together with a pharmaceutically acceptable diluent or carrier.

* * * * *